United States Patent [19]

Bernstein

[11] 4,395,420

[45] Jul. 26, 1983

[54] METHOD AND COMPOSITION FOR TREATING PRURITIS

[76] Inventor: Joel E. Bernstein, 615 Brierhill Rd., Deerfield, Ill. 60015

[21] Appl. No.: 328,955

[22] Filed: Dec. 9, 1981

[51] Int. Cl.³ .................... A61K 31/02; A61K 31/33; A61K 31/135; A61K 31/335
[52] U.S. Cl. .................................. 424/278; 424/244; 424/330; 424/350
[58] Field of Search ........................................ 424/278

[56] References Cited

PUBLICATIONS

Merck Index 9th Ed. (1976) p. 456.

*Primary Examiner*—Stanley J. Friedman
*Attorney, Agent, or Firm*—Emrich & Lee and Brown, Hill, Dithmar, Stotland, Stratman & Levy

[57] ABSTRACT

A method of and composition for treating pruritis comprising topically applying a therapeutically effective amount of a tricyclic anti-depressant in a pharmaceutically acceptable carrier. The tricyclic is present in the range of from about 0.1% to about 10% by weight of the carrier and is applied in divided doses.

16 Claims, No Drawings

METHOD AND COMPOSITION FOR TREATING PRURITIS

BACKGROUND OF THE INVENTION

Itching or pruritis is a common dermatologic symptom. The causes of pruritis are complex and poorly understood. The best understood mechanism of itching is the release of histamine in the skin leading to urticarial wheals and intense itching. Such itching has traditionally been relieved by antihistamines. While antihistamine therapy is often effective, the sedation and drowsiness produced by antihistaminic agents limits their effectiveness.

Many kinds of itching are not however easily relieved by antihistamines. For example, conditions such as Hodgkin's Disease, mycosis fungoides (cutaneous malignancy) and severe jaundice produce intense itching unrelieved by antihistamines. Therefore, there is a need for improved treatment to relieve itching which can not only be an alternative to antihistaminic treatment of itching due to such causes as mosquitoe bites which responds to such treatment, but which further provides relief in intractable cases of pruritis which heretofore have been virtually impossible to treat except as disclosed in my prior U.S. Pat. No. 4,181,726 issued Jan. 1, 1980, a method based on the systemic effect on the central nervous system. The present invention provides such a composition and method independent of systemic effects on the central nervous system.

I have discovered surprisingly that tricyclic anti-depressants usually prescribed for ameliorating the effects of severe depression are effective at relieving itching when applied topically. These compounds include the pharmaceutically acceptable salts of the tricyclics. The term pharmaceutically acceptable salts, as used herein, refers to the physiologically acceptable acid addition salts such as the hydrochloride, hydrobromide, hydroiodide, acetate, valerate, oleate, etc. Doxepin, amitriptyline and imipramine respectively are the tertiary amine derivatives of dibenzoxepin, dibenzocycloheptadiene and dibenzazepine wherein the nitrogen atom is connected to the ring structure by a three carbon aliphatic chain and the tertiary amine has two carbon atoms attached thereto in addition to the aliphatic chain.

The present invention relates to a method and composition for topically treating pruritis.

A principal object of the present invention is topically to apply divided doses of tricyclic anti-depressant compounds traditionally employed systemically for treatment of mental depression to relieve pruritis.

Yet another object of the present invention is to provide a method and composition for treating pruritis wherein the tricyclic anti-depressant contains one of the following ring structures:

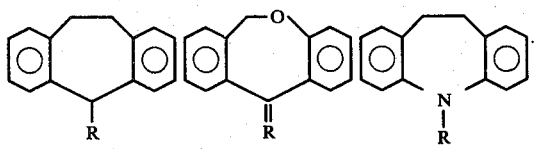

These and other objects of the present invention may be more readily understood when considered in conjunction with the following detailed description and examples.

DETAILED DESCRIPTION OF THE PREFERRED EMBODIMENTS

I investigated the possible antipruritic effects of topically applied formulations containing doxepin hydrochloride, amitriptyline hydrochloride, and imipramine hydrochloride by incorporating such tricyclic anti-depressant compounds into suitable dermatological vehicles and having patients with itchy skin disorders apply such formulations for relief. These topical formulations were surprisingly effective at alleviating many types of pruritis.

In the practice of this invention concentrations of salts of doxepin, amitriptyline and imipramine varying from 0.1% by weight to about 10% by weight, were incorporated into creams, ointments, lotions and solutions and applied to itchy skin in divided doses for the relief of such itching. The preferred amount of active ingredient is from about 0.5% by weight to about 5% by weight of the carrier.

EXAMPLE 1

A topical formulation prepared by incorporating one tenth percent (0.1%) by weight doxepin hydrochloride in unscented cold cream was applied twice daily over a two week period by a 73 year-old woman with moderate itching due to dry skin (xerosis or asteatrosis). The doxepin cream provided some, but not complete relief of the itching during the period of application.

EXAMPLE 2

A solution prepared by incorporating two percent (2%) by weight doxepin hydrochloride in 95% ethanol in water was applied to the mosquito bites of an eleven year-old male. Such applications provided prompt temporary relief of the itching associated with these bites.

EXAMPLE 3

Ten percent (10%) by weight doxepin hydrochloride was incorporated into white petrolatum and applied to the skin of a thirty-six year-old female patient with an itchy eczematous eruption on her arms. The doxepin cream produced dramatic relief of the itching but had to be discontinued after five days due to a possible irritation or sensitization reaction.

EXAMPLE 4

One percent (1%) by weight amitriptyline hydrochloride was incorporated in calamine lotion and applied to an itchy patch of skin on the hands and arms of a thirty-six year-old patient suffering from poison ivy dermatitis. The lotion produced excellent relief of the itching.

EXAMPLE 5

A cream was prepared by compounding five percent (5%) by weight amitriptyline hydrochloride in unscented cold cream and the resulting cream was applied to the itchy perianal area of a patient with pruritus ani. Relief was prompt and was maintained on a 4–5x/day application schedule.

EXAMPLE 6

A two percent (2%) by weight imipramine hydrochloride ointment, prepared by incorporating the active agent in white petrolatum, was applied to the body of a seventy-two year-old male with generalized itching secondary to dry skin (xerosis or asteatosis). Application of this ointment twice daily provided excellent relief of the itching.

It will be apparent to those skilled in the art that only the preferred embodiments have been described by way of exemplification and that there are various modifications which fall within the scope of this invention.

What is claimed is:

1. A method of treating pruritis in humans in need of such treatment comprising topically applying a therapeutically effective amount of doxepin or a physiologically acceptable acid addition salt thereof.

2. The method of claim 1, wherein the doxepin or acid addition salt thereof is present in a pharmaceutically acceptable carrier at a concentration of not less than about 0.1% by weight of the carrier.

3. The method of claim 1, wherein the doxepin or the acid addition salt thereof is present in a pharmaceutically acceptable carrier at a concentration in the range of from about 0.1% by weight to about 10% by weight of the carrier.

4. The method of claim 1, wherein the doxepin or the acid addition salt thereof is present in a pharmaceutically acceptable carrier at a concentration in the range of from about 0.5% by weight to about 5% by weight of the carrier.

5. The method of claim 1, wherein the acid addition salt is selected from the class consisting of halides other than fluoride, acetate, valerate, and oleate.

6. The method of claim 5, wherein the acid addition salt is doxepin hydrochloride and is present in the range of from 0.5% by weight to about 10% by weight of the carrier.

7. The method of claim 1, wherein the carrier is an ointment or cream.

8. The method of claim 1, wherein the carrier is an aqueous-alcohol solution.

9. A composition for treating pruritis comprising a carrier pharmaceutically acceptable for topical application to the skin containing a therapeutic amount of doxepin or a physiologically acceptable acid addition salt thereof.

10. The composition of claim 9, wherein the doxepin or acid addition salt thereof is present in the carrier at a concentration of not less than about 0.1% by weight of the carrier.

11. The composition of claim 9, wherein the doxepin or acid addition salt thereof is present in the carrier at a concentration in the range of between about 0.1% by weight and about 10% by weight of the carrier.

12. The composition of claim 9, wherein the doxepin or acid addition salt thereof is present in a pharmaceutically acceptable carrier at a concentration in the range of from about 0.5% by weight to about 5% by weight of the carrier.

13. The composiition of claim 9, wherein the acid addition salt is selected from the class consisting of halides other than fluoride, acetate, valerate, and oleate.

14. The composition of claim 13, wherein the acid addition salt is doxepin hydrochloride and is present in the range of from 0.5% by weight to about 10% by weight of the carrier.

15. The composition of claim 9, wherein the carrier is an ointment or cream.

16. The composition of claim 9, wherein the carrier is an aqueous-alcohol solution.

* * * * *